March 3, 1970 S. I. SCHWARTZ ET AL Re. 26,810

IMPLANTABLE ELECTRODE FOR NERVE STIMULATION

Original Filed Dec. 10, 1965 2 Sheets-Sheet 1

INVENTORS.
SEYMOUR I. SCHWARTZ
ROBERT C. WINGROVE
JAMES A. ANDERSON
BY Donald R. Stone
ATTORNEY

IMPLANTABLE ELECTRODE FOR NERVE STIMULATION

Original Filed Dec. 10, 1965 2 Sheets-Sheet 2

INVENTORS
SEYMOUR I. SCHWARTZ
ROBERT C. WINGROVE
BY JAMES A. ANDERSON
Donald R. Stone
ATTORNEY United States Patent Office Re. 26,810
Reissued Mar. 3, 1970

26,810
IMPLANTABLE ELECTRODE FOR NERVE STIMULATION

Seymour I. Schwartz, Rochester, N.Y., Robert C. Wingrove, Circle Pines, and James A. Anderson, Minneapolis, Minn., assignors to Medtronics, Inc., Minneapolis, Minn., a corporation of Minnesota Original No. 3,421,511, dated Jan. 14, 1969, Ser. No. 512,981, Dec. 10, 1965. Application for reissue Mar. 5, 1969, Ser. No. 807,460
Int. Cl. A61n *1/04*
U.S. Cl. 128—418 4 Claims

Matter enclosed in heavy brackets [ ] appears in the original patent but forms no part of this reissue specification; matter printed in italics indicates the additions made by reissue.

ABSTRACT OF THE DISCLOSURE

Electrode apparatus for connection to a nerve, having a pair of electrodes partially embedded within a substance inert to body fluids and tissue, the exposed portions of the electrodes lying in a groove generally conformed to the shape of the nerve for providing atraumatic egress of the nerve to the electrode, and including a further connected portion of the material inert to body food and tissue for covering the groove after the electrodes have been connected to space points on the nerve. Coiled leads are connected to the nerve, and are also encased in material inert to body foods and tissue.

This invention relates to medical apparatus, and more particularly to an implantable electrode for electrical stimulation of a single nerve within the body of an animal. The word animal is here used in its broad sense, including Homo sapiens.

Briefly described, the apparatus of this invention comprises a pair of electrodes almost entirely embedded within a substance, such as silicon rubber, which is inert to body fluids and tissue, and is thus suitable for implantation in the body of an animal. A pair of flexible leads are connected to the electrodes and may be used to connect the electrodes to an implanted or external source of electrical signal energy. The leads are also embedded in a substance which acts as an electrical insulator as well as being inert to body fluids and tisue. An exposed portion of each of the electrodes is formed to be connected to spaced points along a single nerve, to provide electrical stimulation of the nerve from the source of signal energy. The electrodes and the leads are also made of a material inert to body fluids and tissue, such as platinum or stainless steel. An extra member of the substance is provided, such as a flap, for tying down over the electrodes after they have been connected to the nerve.

The need for the apparatus of this invention is apparent upon consideration of such modern medical equipment as the carotid sinus nerve stimulator fully described in a co-pending application by Seymour I. Schwartz and Robert C. Wingrove, Ser. No. 397,899, entitled "Implantable Stimulator for Reducing Blood Pressure in Hypertensive Persons." In this co-pending application there is described the use of an implantable, artificial nerve stimulator, which provides electrical impulses for stimulation of the carotid sinus nerve to alleviate the problems of hypertensive animals.

Electrical impulses for major organs of the body of an animal may be transmitted to that organ by means of pointed electrodes which penetrate the body of the organ and indirectly make contact with a nerve network without damaging the organ. Such general stimulation is not effective where the impulse must be superimposed on one particular nerve and that nerve alone. The present structure is designed to allow transmission of an electrical impulse specifically and solely to a selected nerve, such as the carotid sinus nerve or the vagus nerve, by way of example.

Figure 1:
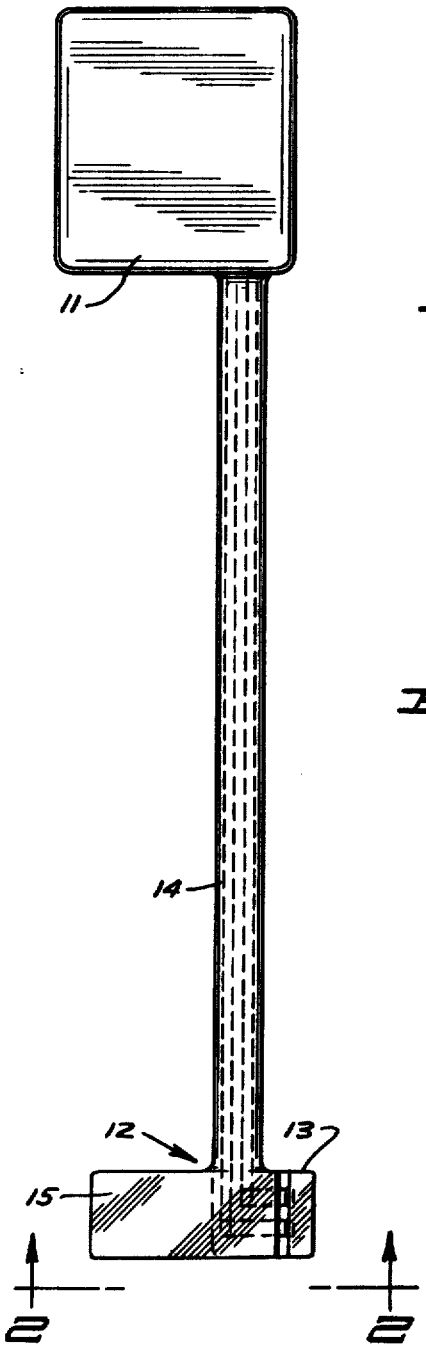
FIG. 1 is a view of a first embodiment of the invention as may be used with an implantable source of electrical signal energy.

FIG. 1 discloses a first embodiment of this invention having a head indicated generally at 12, including an electrode carrying member 13 and a flap member 15. A lead carrying member or trail 14 is connected to head 12. Tail 14 is also shown connected to an implantable source of electrical signal energy 11.

Figure 2:
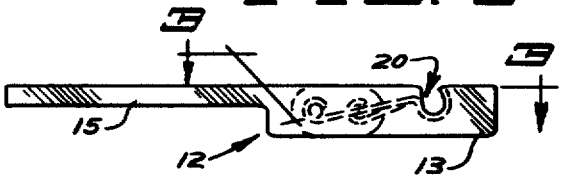
FIG. 2 is a sectional view of FIG. 1 taken along the line 2—2 and showing a hinged flap which may be fastened over a nerve connected to the electrodes.

FIG. 2 is a side view of head 12 showing a groove 20 in member 13, and showing flap 15 folded over and connected to member 13.

Figure 3:
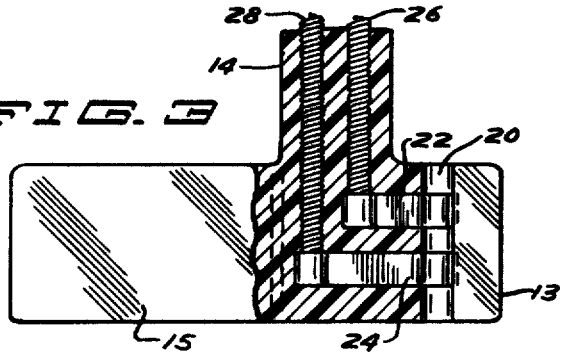
FIG. 3 is a sectional view of FIG. 2 taken along the line 3—3.

FIG. 3 discloses a pair of electrodes 22 and 24 partially encapsulated in member 13 and formed into the groove 20. A pair of leads 26 and 28, here shown as coiled lengths of an electrically conductive material, are connected, respectively, to electrodes 22 and 24. Leads 26 and 28 are also encapsulated in the substance of tail 14.

Figure 4:
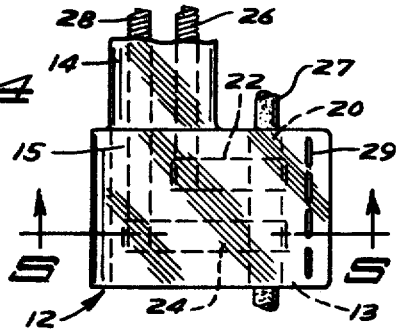
FIG. 4 is a plan view of the first embodiment of this invention showing th e flap fastened over the electrodes connected to a nerve.

FIG. 4 discloses electrodes 22 and 24 connected to spaced points along a nerve 27 in groove 20. Flap 15 is shown folded over to cover and thus insulate electrodes 22 and 24 and nerve 27 in groove 20. Flap 15 is fastened to member 13 by use of sutures 29.

Figure 5:
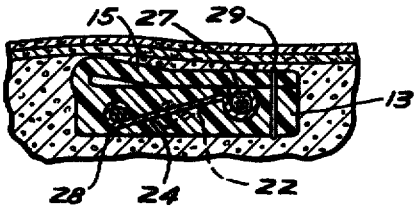
FIG. 5 is a sectional view of FIG. 4 taken along the line 5—5.

FIG. 5 also discloses the nerve 27 as covered over by the flap 15 fastened to member 13 by sutures 29.

Figure 6:
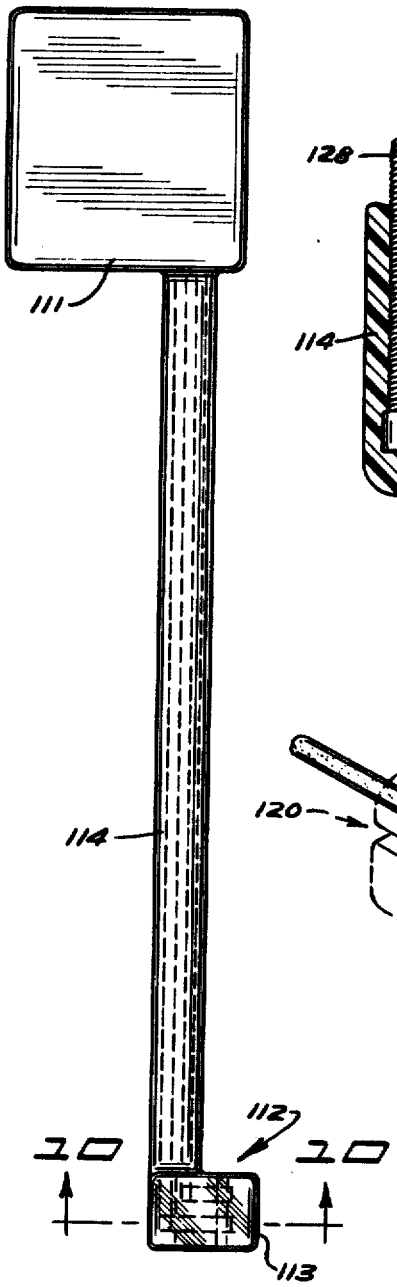
FIG. 6 is a view of a second embodiment of this invention also connected to the implantable source of electrical signal energy.

FIG. 6 discloses a second embodiment of this invention having a head indicated generally at 112, a tail 114 connected to head 112 and also connected to a source of electrical signal energy 111.

Figure 7:
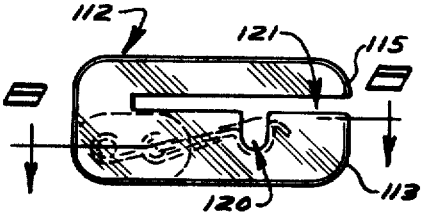
FIG. 7 is a sectional side view of the second embodiment of this invention showing the head of the second embodiment having a slot forming an upper and lower layer.

FIG. 7 is a side view of head 112 disclosing a slot 121 cut in head 112 to form an upper layer 115 and a lower layer 113. A groove 120 is shown in lower layer 113.

Figure 8:
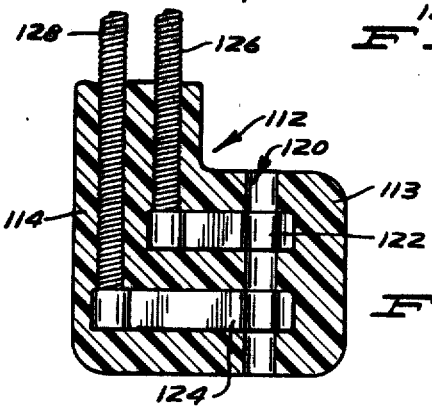
FIG. 8 is a sectional view of FIG. 7 taken along the line 8—8.

FIG. 8 discloses a pair of electrodes 122 and 124 partially encapsulated in the substance of lower layer 113, and partially formed to groove 120. A pair of leads 126 and 128, here shown as coiled lengths of an electrically conductive material, are connected, respectively, to electrodes 122 and 124. Leads 126 and 128 are encapsulated in the substance of tail 114.

Figure 9:
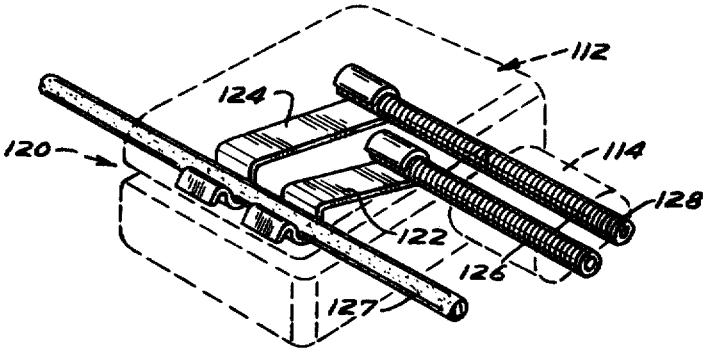
FIG. 9 is a perspective view of the second embodiment of this invention.

FIG. 9 is a perspective view which discloses electrodes 122 and 124 connected to spaced points along the length of a nerve 127.

FIG. 10 again shows nerve 127 within the groove 120 with upper layer 115 fastened to lower layer 113 by sutures 129.

Since this invention comprises electrodes which are to be implanted within the body of an animal, it is necessary that the substance which comprises head 12 and 112 and tail 14 and 114, be inert to body fluids and tissue. Such a substance which has been successfully used is silicon rubber. It is also necessary that electrodes 22 and 24, and 112 and 124, which must connect directly to the outer wall of a nerve 27 or 127, be of a material inert to body fluids and tissue and be not harmful to the outer wall of the nerve to which they are attached. Such a material which has been successfully used is platinum. Another material which may also be used is stainless steel. Leads 26 and 28, and 126 and 128 must also be of a material inert to body fluids and tissue. It may be desirable, but is not mandatory that leads 26 and 28, and 126 and 128, be of the same material as electrodes 22 and 24, and 122 and 124.

The leads in the embodiments here shown are disclosed as being coiled lengths of a material, to facilitate ease of flexibility. This has proven to be a highly desirable type of lead structure, but it is not intended that this entire invention be limited to such a lead structure.

Figure 10:
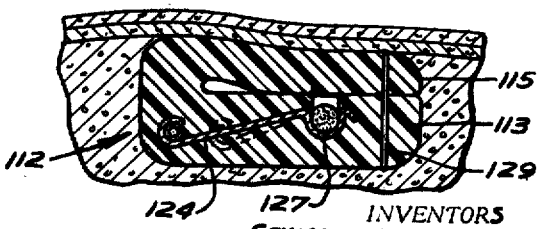
FIG. 10 is a sectional view of the drawing of FIG. 6 taken along the line 10—10.

While it is necessary that a portion of electrodes 22 and 24, and 122 and 124, not be encapsulated in the substance of head 12 so that the electrodes may be connected to nerve 27 or 127, it is highly undesirable to leave the electrodes exposed after connection to the nerve. To overcome this problem the embodiments of this invention provide either a flap 15 or an upper layer 115. As shown in FIGS. 4 and 5, flap 15 may be folded over to cover electrodes 22 and 24 when they are connected to nerve 27. Flap 15 is then fastened to member 13, such as by sutures 29. As shown in FIGS. 7, 9 and 10, upper layer 115 is separated from lower layer 113 only by the width of slot 121. When electrodes 122 and 124 have been connected to nerve 127, upper layer 115 may be fastened down upon them by means such as sutures 29.

Groove 20 in member 13, and groove 120 in lower layer 113, are shaped generally to the configuration of nerves 27 and 127, respectively, and also facilitate firm fastening and insulation of the connection of the electrodes to the nerves.

The sources of electrical signal energy 11 and 111, shown in FIGS. 1 and 6, respectively, may be transistorized blocking oscillators powered by long life [rechangeable] *rechargeable* batteries, which provide pulses at a predetermined frequency to the nerves 27 and 127, respectively. Though the sources 11 and 111 shown here are implantable, that is, are encapsulated in a substance inert to body fluids tissue for implantation in the body of an animal, it is not mandatory that the electrode apparatus of this invention be used with an implantable source of electrical signal energy. The tails 14 and 114, including leads 26 and 28, and 126 and 128, respectively, may extend from within the body to a point external to the body, and be connected to any one of a number of sources of electrical signal energy. Also, the leads may extend to a circuit implanted in the body but powered from a source external to the body.

The electrode apparatus of this invention has been successfully implanted in a human being, and shown to be fully operable in providing electrical impulse stimulation to a carotid sinus nerve in one case and to a vagus nerve in a second case. In the various embodiments successfully used, silicon rubber was used as the substance to encapsulate the leads and electrodes. In at least one such embodiment the electrodes were made of platinum, while the leads were made of coiled lengths of stainless steel.

It is apparent from the foregoing description that the apparatus of this invention provides a [noved] *novel* structure for connection of a source of signal energy to a single nerve, to provide artificial stimulation of that nerve by timed electrical impulses from the source of signal energy. Further, the apparatus of this invention has been used and has been successful in alleviating medical problems of human beings.

The embodiments of the invention in which an exclusive property or privilege is claimed are defined as follows:

1. Electrode apparatus implantable in the body of an animal for stimulation of a single nerve comprising:
   - a housing of an electrically insulating substance substantially inert to body fluids and tissue, said housing having a head and a tail extending therefrom;
   - a slot in said head dividing a part of said head into an upper layer and a lower layer;
   - a groove in said lower layer adjacent said slot;
   - a pair of electrodes of an electrically conductive material substantially inert to body fluids and tissue, and encased in said head of said housing in spaced relation to one another;
   - a portion of each of said pair of electrodes formed to and fitted in said groove, said portions adapted to be connected to spaced points on a single nerve in the body of an animal;
   - said upper layer of said housing adapted to be fastened to said lower layer to hold and shield the single nerve in contact with said pair of electrodes;
   - a pair of leads of said material encased in said tail of said housing; and
   - each of said pair of leads connected to a different one of said pair of electrodes, for connecting said pair of electrodes to a source of signal energy for stimulating the single nerve.

2. Medical apparatus for implantation into the body of an animal comprising:
   - first and second electrodes of an electrically conductive material substantially inert to body fluids and tissue;
   - first and second leads of said material connected, respectively, to said first and second electrodes, and adapted to be connected to a source of electrical signal energy;
   - a first portion of said first and second electrodes and said first and second leads being encapsulated in a housing of an electrically insulating substance substantially inert to body fluids and tissue;
   - a second portion of said first and second electrodes adapted to be connected to spaced points along a single nerve in the body of an animal, for stimulation of the single nerve upon receipt of a signal from the source of signal energy; and
   - a further member of said substance flexibly connected to said housing for fastening over said second portion of said first and second electrodes when connected to the single nerve.

*3. Electrode apparatus implantable in the body of an animal for stimulation of a single nerve comprising:*
   - *a housing of an electrically insulating substance substantially inert to body fluids and tissue, said housing having a head and a tail extending therefrom;*
   - *a slot in said head dividing a part of said head into an upper layer and a lower layer;*
   - *a groove in said lower layer adjacent said slot;*
   - *a pair of electrodes of an electrically conductive material substantially inert to body fluids and tissue, and encased in said head of said housing in spaced relation to one another;*
   - *a portion of each of said pair of electrodes formed to and fitted in said groove, said portions adapted to be connected to spaced points on a single nerve in the body of an animal;*
   - *said upper layer of said housing adapted to be fastened to said lower layer to hold and shield the single nerve in contact with said pair of electrodes;*
   - *a pair of leads of an electrically conductive material substantially inert to body fluid and tissue encased in said tail of said housing; and*

*each of said pair of leads connected to a different one of said pair of electrodes, for connecting said pair of electrodes to a source of signal energy for stimulating the single nerve.*

*4. Medical apparatus for implantation into the body of an animal comprising:*

*first and second electrodes of an electrically conductive material substantially inert to body fluids and tissue;*

*first and second leads of an electrically conductive material substantially inert to body fluids and tissue connected, respectively, to said first and second electrodes, and adapted to be connected to a source of electrical signal energy;*

*a first portion of said first and second electrodes and said first and second leads being encapsulated in a housing of an electrically insulating substance substantially inert to body fluids and tissue;*

*a second portion of said first and second electrodes adapted to be connected to spaced points along a single nerve in the body of an animal, for stimulation of the single nerve upon receipt of a signal from the source of signal energy; and*

*a further member of said substance flexibly connected to said housing for fastening over said second portion of said first and second electrodes when connected to the single nerve.*

References Cited

The following references, cited by the Examiner, are of record in the patented file of this patent or the original patent.

UNITED STATES PATENTS

| | | | |
|---|---|---|---|
| 3,157,181 | 11/1964 | McCarty | 128—404 |
| 3,348,548 | 10/1967 | Chardock | 128—418 |

OTHER REFERENCES

Glass et al.: "American Heart Journal," vol. 67, No.1, January 1964, pp. 137–139.

WILLIAM E. KAMM, Primary Examiner

UNITED STATES PATENT OFFICE

CERTIFICATE OF CORRECTION

Patent No. Re. 26,810 Dated March 3, 1970

Inventor(s) S. I. Schwartz et al

It is certified that error appears in the above-identified patent and that said Letters Patent are hereby corrected as shown below:

Column 1, line 5, change "Medtronics, Inc." to --Medtronic, Inc.--.

In the Abstract of the Disclosure, column 1, line 25, change "food" to --fluids--; line 27, change "space" to --spaced--; line 29, change "foods" to --fluids--.

Column 2, line 16, change "th e" to --the--.

Column 3, line 53, between "fluids" and "tissue" insert --and--.

Column 4, line 74, change "fluid" to --fluids--.

SIGNED AND
SEALED
DEC 1 - 1970

(SEAL)
Attest:

Edward M. Fletcher, Jr.
Attesting Officer.

WILLIAM E. SCHUYLER, JR.
Commissioner of Patents